(12) United States Patent
Johnson et al.

(10) Patent No.: US 12,296,187 B2
(45) Date of Patent: May 13, 2025

(54) PHOTOBIOMODULATION THERAPY TO IMPROVE FUNCTIONAL MOBILITY OF STROKE SURVIVORS

(71) Applicant: MULTI RADIANCE MEDICAL, Solon, OH (US)

(72) Inventors: Douglas Johnson, Brownstown, MI (US); Max Kanarsky, Solon, OH (US); Ernesto Cesar Pinto Leal, Jr., Sao Paulo (BR)

(73) Assignee: MEDICAL QUANT USA INC., Solon, OH (US)

( * ) Notice: Subject to any disclaimer, the term of this patent is extended or adjusted under 35 U.S.C. 154(b) by 972 days.

(21) Appl. No.: 17/294,811

(22) PCT Filed: Nov. 4, 2019

(86) PCT No.: PCT/US2019/059603
§ 371 (c)(1),
(2) Date: May 18, 2021

(87) PCT Pub. No.: WO2020/106439
PCT Pub. Date: May 28, 2020

(65) Prior Publication Data
US 2022/0001194 A1 Jan. 6, 2022

Related U.S. Application Data

(60) Provisional application No. 62/770,402, filed on Nov. 21, 2018.

(51) Int. Cl.
*A61N 5/06* (2006.01)
*A61N 2/00* (2006.01)
*A61N 5/067* (2006.01)

(52) U.S. Cl.
CPC .......... *A61N 5/0613* (2013.01); *A61N 2/002* (2013.01); *A61N 2/004* (2013.01); *A61N 5/067* (2021.08);
(Continued)

(58) Field of Classification Search
CPC .. A61N 2/002; A61N 2/00; A61N 2005/0667; A61N 2005/0666;
(Continued)

(56) References Cited

U.S. PATENT DOCUMENTS 5,464,436 A * 11/1995 Smith ................. A61N 5/0616
606/9
2005/0228463 A1 * 10/2005 Mac ..................... A61N 5/0619
607/89
(Continued)

FOREIGN PATENT DOCUMENTS

WO 2018191640 A1 10/2018

OTHER PUBLICATIONS

International Search Report dated Feb. 23, 2020 for Application No. PCT/US2019/59603.

*Primary Examiner* — Samuel G Gilbert
(74) *Attorney, Agent, or Firm* — Tarolli, Sundheim, Covell & Tummino LLP

(57) ABSTRACT

Photobiomodulation therapy (PBMT) can be used to improve functional mobility of stroke survivors. A light source device can be contacted to a subject's skin proximal to an area of hemiplegia within a subject due to the stroke. A light signal (with wavelengths from the red to infrared part of the spectrum) can be applied in at least one of a pulsed operating mode, a continuous operating mode, and a super-pulsed operating mode through the light source device to the area of hemiplegia. The light signal is applied for a time sufficient to stimulate a phototherapeutic response in the (Continued)

area of hemiplegia to improve the functional mobility of the subject.

14 Claims, 8 Drawing Sheets

(52) U.S. Cl.
CPC ............... *A61N 2005/0659* (2013.01); *A61N 2005/0663* (2013.01)

(58) Field of Classification Search
CPC .... A61N 2005/0665; A61N 2005/0664; A61N 2005/0663; A61N 2005/0662; A61N 2005/0661; A61N 2005/0659; A61N 2005/0658; A61N 2005/0652; A61N 2005/0651; A61N 2005/065
See application file for complete search history.

(56) References Cited

U.S. PATENT DOCUMENTS

| | | | |
|---|---|---|---|
| 2011/0066213 A1* | 3/2011 | Huttermann | A61N 5/0613 607/88 |
| 2015/0112411 A1 | 4/2015 | Beckman et al. | |
| 2016/0129281 A1* | 5/2016 | Kim | A61N 5/0622 607/90 |

\* cited by examiner ns

PHOTOBIOMODULATION THERAPY TO IMPROVE FUNCTIONAL MOBILITY OF STROKE SURVIVORS

CROSS-REFERENCE TO RELATED APPLICATIONS

This application claims the benefit of U.S. Provisional Application No. 62/770,402, filed Nov. 21, 2018, entitled "PHOTOBIOMODULATION THERAPY TO IMPROVE SYMPTOMS OF STROKE". This provisional application is hereby incorporated by reference in its entirety for all purposes.

TECHNICAL FIELD

The present disclosure relates generally to photobiomodulation therapy (PBMT) and, more specifically, to systems and methods that use PBMT to improve functional mobility of stroke survivors.

BACKGROUND

Cerebrovascular accidents (referred to as "strokes"), defined as an interruption in the blood supply to the brain when an artery is blocked or ruptured, are among the main causes of disability and death in the adult population worldwide. Hemiplegia (weakness or paralysis on one side of the body) affects approximately 88% of stroke survivors and is characterized by muscle fatigue, spasticity, stiffness, and joint pain, leading to body asymmetry and difficulty in transferring weight to the paretic side. The impaired limb function affects the ability to maintain postural and motor control, leading to impaired gait, loss of balance, and reduced functional mobility. Indeed, more than 80% of stroke survivors have limitations in daily living due to reduction in functional mobility.

SUMMARY

The present disclosure relates to improving functional mobility of stroke survivors using photobiomodulation therapy (PBMT). PBMT provides a non-pharmacological tool that can be used alone or in combination with medications and/or rehabilitative therapy to enhance the functional mobility of stroke patients with the goal of making daily activities easier.

In one aspect, the present disclosure can include a method for improving functional mobility of stroke survivors. A light source device can be contacted to a subject's skin proximal to an area of hemiplegia within a subject due to a stroke. A light signal can be applied in at least one of a pulsed operating mode, a continuous operating mode, and a super-pulsed operating mode through the light source device proximal to an area of hemiplegia within the subject due to the stroke. The light signal is applied for a time sufficient to stimulate a phototherapeutic response in at least one muscle proximal to the area of hemiplegia within the subject due to the stroke.

In another aspect, the present disclosure can include a light source device configured to contact a subject's skin proximal to an area of hemiplegia within a subject due to a stroke. The light source device includes a cluster of light delivery sources, a permanent magnet, a processing unit, and a power source. The cluster of light delivery sources can include: a first light source configured to generate a first portion of a light signal with a wavelength from 890-910 nm in a super-pulsed operating mode; a second light source configured to generate a second portion of the light signal with a wavelength from 600-700 nm in a pulsed operating mode or a continuous operating mode; and a third light source configured to generate a third portion of the light signal with a wavelength from 810-880 in the pulsed operating mode or the continuous operating mode. The permanent magnet can provide a constant magnetic field from 5 mT to 1 T. The processing unit can be preprogrammed with a time for application of the light signal to the area of hemiplegia.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
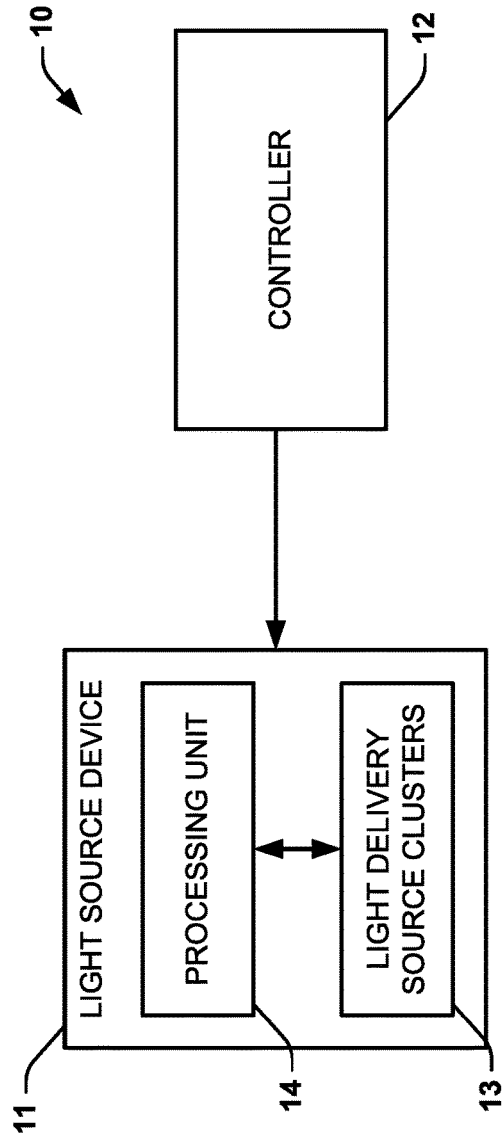
FIG. 1 is a block diagram illustration showing an example of a system that configures and applies photobiomodulation therapy (PBMT) proximal to an area of hemiplegia within a subject due to a stroke to increase functional mobility in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the terms "stroke" and "cerebrovascular accident" refer to an interruption in the blood supply to the brain when an artery is blocked or ruptured. A stroke can be, for example, an ischemic stroke, a hemorrhagic stroke, or the like.

As used herein, the term "hemiplegia", also referred to as "hemiparesis" and "hemiparalysis", can refer to weakness and/or paralysis of at least a portion of one side of the body that is common in stroke victims. Hemiplegia can relate to loss of motor function, resulting in various degrees of impairment or disability.

As used herein, the term "functional mobility" can refer to the manner in which a person is able to move around in the environment in order to participate in the activities of daily living (e.g., standing, bending, walking, climbing, etc.). Functional mobility can be limited due to muscle weakness, spasticity, joint pain, or the like, which may be caused by hemiparalysis.

As used herein, the term "photobiomodulation" refers to the application of a light signal to a portion of a subject's body to induce a phototherapeutic response in cells within the portion of the subject's body.

As used herein, the term "photobiomodulation therapy (PBMT)" refers to a drug-free, non-invasive treatment procedure, in which a light signal is applied to a certain region of a subject's body to treat a certain medical condition (e.g., pain, injury, disorder, disease, or the like) via a phototherapeutic response. In some instances, PBMT can be used alone to induce a phototherapeutic response, but in other instances, PBMT can be used in combination with medications and/or alternative rehabilitative therapies to achieve a more favorable treatment outcome.

As used herein, the term "light signal" refers to light having at least one wavelength. However, the light signal may include a combination of lights having wavelengths that create a synergistic effect when combined and improve the percentage of available light at greater tissue depths. In some instances, the wavelengths can be within a wavelength range of 600-1100 nm. For example, the wavelengths can include at least one wavelength corresponding to the visible range of the electromagnetic spectrum (e.g., red light) and at least one wavelength corresponding to the near-infrared or infrared range of the electromagnetic spectrum.

As used herein, the term "light source device" refers to a mechanical implement that can deliver a light signal of PMBT to a portion of the subject's body (an area of hemiplegia within a subject due to a stroke). Examples of the light source device include a probe, a flexible array device, or the like.

As used herein, the term "light source" refers to a component of a light source device that delivers one or more lights of different wavelengths. For example, the light source can be a low-level laser source (e.g., a laser light emitting diode (LED)) that generates coherent light. The low-level laser source can operate in a super pulsed mode that generates ultrashort pulses with a high peak power and minimal heat. As another example, the light source can be an incoherent light source, such as a traditional LED or light bulb. The incoherent light source can operate in a pulsed mode and/or a continuous mode.

As used herein, the term "phototherapeutic response" refers to a biological response to application of PBMT to a portion of the subject's body (an area of hemiplegia within a subject due to a stroke). The biological response can include one or more of the strengthening of one or more muscles (causing contraction and/or inhibiting contraction) proximal to an area of hemiplegia, increasing or otherwise modulating nerve conduction proximal to the area of hemiplegia, or the like.

As used herein, the term "proximal" refers to a location that is near a target. For example, a device that is located proximal to an area of hemiplegia within a subject due to a stroke can be located over the area of hemiplegia, but need not be directly over the center of the area of hemiplegia.

As used herein, the term "sufficient" refers to an amount adequate enough to satisfy a condition. For example, "a time sufficient to stimulate a phototherapeutic response in an area of hemiplegia" can refer to a light signal being applied to the area of hemiplegia for a time adequate enough to stimulate the phototherapeutic response.

As used herein, the term "direct" refers to the absence of intervening elements. For example, a device that directly contacts a skin surface has no intervening elements between the device and the skin surface. When the term "contact" is used herein, it means "direct contact" unless otherwise stated.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure describes systems and methods that use photobiomodulation therapy (PBMT) to improve functional mobility of stroke survivors. A stroke is caused by an interruption of the blood supply to the brain and occurs when an artery is blocked or ruptures. One of the most common manifestations of a stroke is hemiplegia, which results in a loss of motor function in at least a portion of the body, resulting in various degrees of impairment or disability, which results in a loss of functional mobility. PBMT can be used alone or in combination with traditional rehabilitative techniques to improve the lost functional mobility in stroke survivors.

PBMT provides a non-pharmacological therapy to stroke survivors suffering from hemiplegia, which impairs functional mobility. By applying PBMT proximal to one or more areas of hemiplegia through the stroke survivor's skin in a transcutaneous and non-invasive manner, the PBMT can counteract the effects of the hemiplegia and improve the stroke survivor's functional mobility and overall quality of life. The PBMT can be used to increase the strength of muscles within the area of hemiplegia and/or regulate firing of nerves associated with areas affected by the hemiplegia.

III. Photobiomodulation Therapy (PBMT)

PBMT provides a non-pharmacological therapy that can be administered to a patient in a non-invasive manner to stimulate a phototherapeutic response. As used herein, a light signal is applied through the skin of a patient who has experienced a stroke, to an area oh hemiplegia due to the stroke, to stimulate a phototherapeutic response. In this case, the phototherapeutic response can include a biological response leading to one or more of the strengthening of one or more muscles (causing contraction and/or inhibiting contraction) proximal to an area of hemiplegia, increasing or otherwise modulating nerve conduction proximal to the area of hemiplegia, or the like.

While not wishing to be bound by theory, there is strong evidence to suggest that one of the basic mechanisms of PBMT is the acceleration of electron transfer by electromagnetic radiation in the visible and near infrared region of the spectrum, via the modulation of cytochrome c-oxidase (CCO) activity. Traditionally, PBMT has attempted to modulate CCO activity using a single wavelength in the visible and near infrared region of the spectrum. However, the use of such single wavelengths cannot effectively modulate CCO activity since the single wavelength is limited by its specific absorption spectrum. The light signal used herein has a combination of wavelengths, which are used concurrently, providing an overlapping effect of peak activation, which accelerates CCO activity. Additionally, the time of CCO activation is prolonged across the entire therapeutic window by delivering much smaller doses across many wavelengths, rather than a single wavelength of a greater power. The multiple wavelengths enhance adenosine triphosphate (ATP) production, requiring less energy, and provides continual photodissociation of nitric oxide (NO), not only from CCO, but also from intracellular stores like nitrosylated forms of hemoglobin and myoglobin. NO is a potent vasodilator and PBMT can increase the vasodilation due to NO and increases the availability of oxygen to treated cells, and allows for greater traffic of immune cells into tissue, which counteracts inflammatory and immune responses and treats fibromyalgia.

Accordingly, the light signal of the present disclosure includes a combination of individual light waves. The combination enhances each individual wavelength's ability to penetrate the skin, to allow for a greater portion of the available light energy to reach biological targets beneath the surface. Accordingly, the light signal can be configured so that individual light waves (from chosen light sources, with a selected wavelength, with a given power, and the like) within the light signal work constructively to create a synergistic effect. The light signal can be delivered by a light source device that includes a combination of one or more super pulsed lasers (which deliver a desired peak power from an ultrashort pulse with a minimized level of heat accumulated in the patient's tissue), one or more infrared emitting diodes, and one or more light emitting diodes. In some instances, the light source device can include groups of a super pulsed laser, an infrared emitting diode, and a light emitting diode. In other instances, the light source device can include groups of a super pulsed laser, at least three infrared emitting diodes, and at least three light source devices. The use of a super pulsed source can minimize the photo-thermal effect accumulating within the skin surface and target tissue. Additionally, the light source device can include a permanent magnet to provide a static (or constant) magnetic field.

IV. Systems

One aspect of the present disclosure can include a system 10 (FIG. 1) that configures and applies photobiomodulation therapy (PBMT) proximal to an area of hemiplegia within a subject due to a stroke to increase functional mobility. Many stroke survivors experience hemiplegia, weakness or paralysis on one side of the body, characterized by muscle fatigue, spasticity, stiffness, and joint pain, leading to body asymmetry and difficulty in transferring weight to the paretic side affecting the ability to maintain postural and motor control, leading to impaired gait, loss of balance, and reduced functional mobility. Sufferers of hemiplegia have limitations in daily living due to reduction in functional mobility. The PBMT applied by the system 10 can improve the functional mobility of a stroke survivor.

In response to the PBMT, one or more nerves and/or muscles within the area of hemiplegia can undergo a phototherapeutic response, which can help to improve the stroke patient's functional mobility. The phototherapeutic response can lead to increased conduction within the nerves and/or the muscles, thereby reducing the incidence and/or effects of hemiplegia. For example, the increased conduction in the nerves and/or muscles can strengthen muscles, reduce stiffness and spasticity, and/or increase the ability to control muscles affected by hemiparesis. Accordingly, the PBMT of the system 10 can improve the functional mobility of a stroke survivor, thereby improving the subject's overall quality of life. While PBMT is a non-pharmacological therapy that can be used alone to treat hemiplegia, PBMT can also be used in combination with a pharmaceutical treatment and/or an alternative treatment (like rehabilitative exercise) to treat hemiplegia.

The system 10 can include at least a light source device 11 that delivers the PBMT to the area of hemiplegia and a controller 12 to deliver inputs to the light source device 11 related to the delivery of the PBMT via a wired connection and/or a wireless connection. The PBMT can be applied to the area of hemiplegia by a light signal that is generated by a light source device 11. To facilitate the delivery of the light signal to the area of hemiplegia, the light source device 11 can be shaped so that at least a portion makes contact with the subject's skin proximal to the area of hemiplegia.

Figure 7:
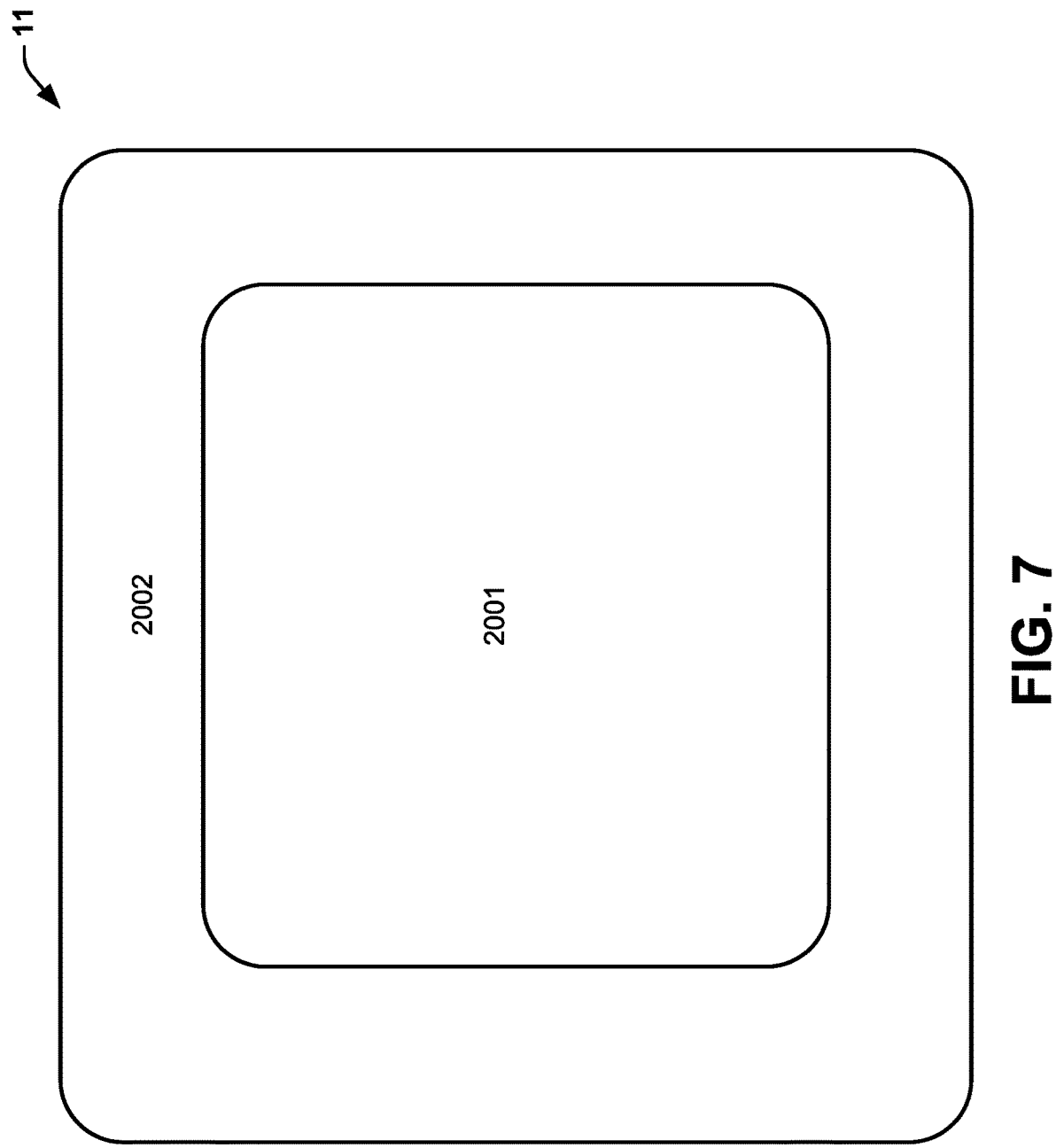
FIG. 7 shows a diagram of an example of the light source device of FIG. 1.

The light source device 11 can be configured in any shape that facilitates contacting a portion of the skin and/or the delivery of the light signal. An example of the light source device 11, including an electronics housing 2001 and a device housing 2002, is shown in FIG. 7. The electronics housing 2001 can include processing unit 14 and the power source and other electronics required for operation of the light source device 11. The device housing 2002 can surround the electronics housing and stabilize the electronics housing 2001. In some instances, the device housing 2002 can embody a securing mechanism to removeably secure the light source device 11 to an area of the subject's skin. For example, the securing mechanism can be able to be disconnected to facilitate movement of the light source device 11. Even in the absence of the securing mechanism, the light source device 11 can be portable with at least a portion being able to be moved to different areas of the subject's body. Light delivery source clusters 13 can be within the electronics housing 2001 and/or within the device housing 2002.

Figure 8:
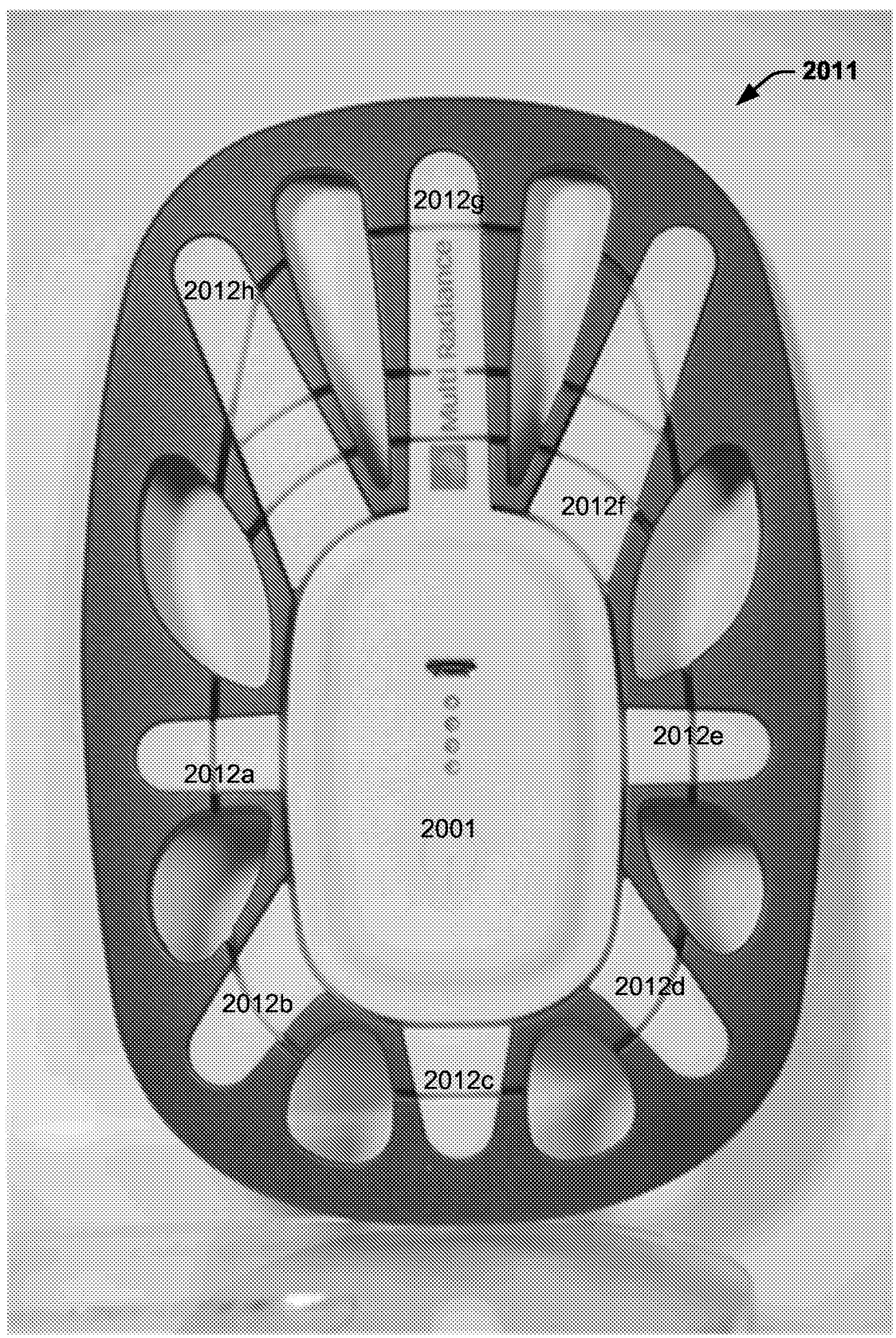
FIG. 8 shows a picture of another example of the light source device of FIG. 1.

As one example, the light source device 11 can be embodied as an insert. The insert can include the electronics housing 2001 and a number of flanges 2012a-h extending from the device housing. Any number of flanges 2012a-h may exist, from 0 to N, where N is an integer limited only by the size of the insert. The electronics housing 2001 and/or the flanges can be made of a hard material (e.g., plastic) and/or a flexible material (e.g., silicone, rubber, neoprene, or the like) and configured with a shape or flexible into a shape that conforms to the target area of hemiplegia. The insert can be inserted into a device housing 2002 as shown in FIG. 8. The device housing 2002 can be made of a flexible material (e.g., silicone, rubber, neoprene, or the like) and secured around an area of the subject's body that includes the area of hemiplegia.

Figure 9:
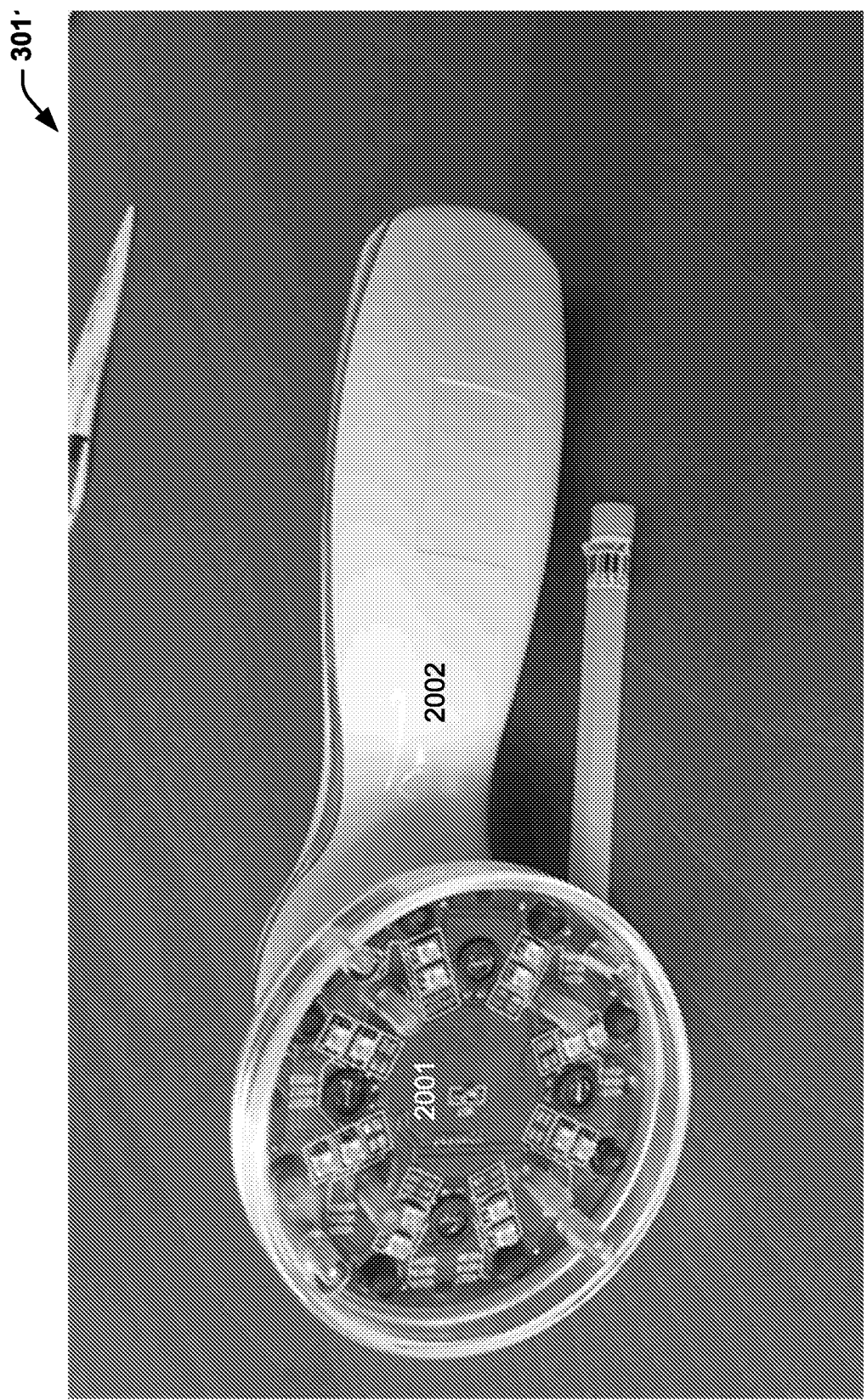
FIG. 9 shows a picture of another example of the light source device of FIG. 1.

As another example, the light source device 11 can be embodied as a probe device 3011 (FIG. 9). The probe device 3011 can include a device housing 22 that is made of a hard material (e.g., a plastic) and include a portion configured to contact the subject's skin proximal to the area of hemiplegia at a 90-degree angle to deliver the light signal. The electronics housing 2001 can be housed within the device housing 2002 with at least the light delivery source clusters 13 being included in an area that contacts the skin. Another example, although not illustrated, can include a flexible array device with a portion shaped to contact the skin at a 180-degree angle to deliver the light signal.

The light source device 11 can include at least one light delivery source to generate the light signal at a certain wavelength, with a certain power, in an operating mode. The operating mode can be at least one of a pulsed operating mode, a continuous operating mode, and a super-pulsed operating mode (delivering high powered light in billionth of a second pulses). The light source device 11 can also include a processing unit 14 programmed (e.g., preprogrammed, programmed in response to an input from the controller 12 (which may be in response to an input), or the like) with a time for application of the light signal to the area of hemiplegia (e.g., the time can be sufficient to stimulate the phototherapeutic response in the area of hemiplegia). The processing unit 14 can also be programmed with the certain wavelength, the certain power, and/or the operating mode. In some instances, the light source device 11 can also include a permanent magnet to provide a static (or constant) magnetic field, which can be used to secure the light source device 11 to the area of the subject's skin and/or to affect the light signal. The constant magnetic field can be from 5 mT to 1 T. Additionally, the light source device 11 can also include a power source. The power source, in some instances, can be an internal battery. In other instances, the power source can receive and/or store power from an external source. In some instances, the external source can be associated with the controller 12.

In some instances, the light signal can include a light wave at a single wavelength of light delivered in a certain operating mode. However, in other instances, the light signal can include a combination of a plurality of individual light waves with different wavelengths of light delivered in two or more different operating modes. The combination of individual light waves is advantageous because the individual light waves can work constructively to create a synergistic effect, enhancing each individual wavelength's ability to penetrate the skin, allowing for a greater portion of the available light energy to reach biological targets beneath the surface of the skin.

Figure 2:
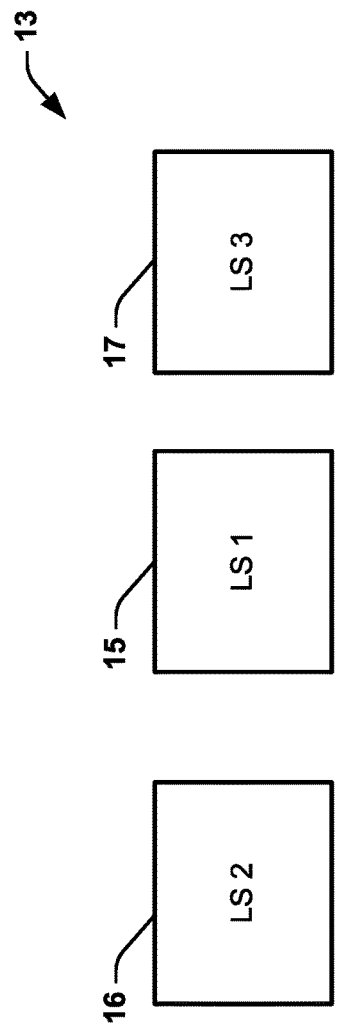
FIG. 2 is a block diagram illustration showing an example configuration of light sources within the light delivery source cluster of FIG. 1.

The plurality of individual light waves can be generated by a plurality of light delivery sources. Accordingly, the light source device 11 can include a plurality of light delivery sources, each configured to deliver light of a certain wavelength, with a given power, in a pulsed operating mode, a continuous operating mode, or a super-pulsed operating mode. One organization of the plurality of light delivery sources is in one or more light delivery source clusters 13 (an example of an individual cluster is shown in FIG. 2). In practice, the light source device can have any number of light delivery source clusters 13, limited only by the size of the area of the light source device 11 designated for delivery of the light signal.

As shown in FIG. 2, each light delivery source cluster 13 includes three types of light sources (LS1 15, LS2 16, LS3 17). However, the light delivery source clusters 13 may include a greater or fewer number of light sources. Three light sources are shown for simplicity of illustration and explanation. The light sources (LS1 15, LS2 16, LS3 17) each generate light waves with wavelengths within a wavelength range of 600-1100 nm (red to infrared). More particularly, LS1 15 can be configured to generate a first portion of the light signal with a wavelength from 890-910 nm (infrared); LS2 16 can be configured to generate a second portion of the light signal with a wavelength from 600-700 nm (red); and LS3 17 can be configured to generate a third portion of the light signal with a wavelength from 810-910 nm. In this example, LS1 15, which is in the middle of each light delivery source cluster 13, can operate in the super-pulsed operating mode, while LS2 16 and LS3 17, which surround LS1, can each operate in the continuous operating mode or the pulsed operating mode. In other words, LS1 can be a super pulsed laser that creates an impulse of high intensity that emits for a billionth of a second in synchrony with LS2 (a red source, like a red LED or a red light) and/or LS3 (an infrared source, like an infrared LED or an infrared light). Advantageously, the use of the super-pulsed laser (LS1) allows a desired peak power to be delivered for an ultrashort pulse with a minimized level of heat accumulated in the subject's skin and area of hemiplegia (in other words, minimizes the photothermal effect).

Many configurations of each light delivery source cluster 13 are possible. Two examples of possible configurations are set forth, but countless other possibilities exist (including with other light sources), as long as there are one or more L1, one or more L2, one or more L3. One possible configuration of each light delivery source cluster 13 is a 1:1:1 configuration, with L1 (the super-pulsed laser) between L2 (the red source) and L3 (the infrared source). Another possible configuration of each light delivery source cluster 13 is a 1:3:3 configuration with L1 surrounded by three (or more) L2 and three (or more) L3. For example, in this configuration, L2 and L3 can alternate as they are arranged around L1 (e.g., L2 L3 L2 L3 L2 L3 surrounding L1). As another example, L2 and L3 can be grouped together around L1 (e.g., L2 L2 L2 L3 L3 L3). Although not expressly described, other example configurations are possible in the 1:3:3 light delivery source cluster 13. The light delivery source clusters 13 within the same light source device 11 can be configured identically, but need not have identical configurations. For example, a light source device 11 can have three light delivery source clusters, with one a 1:1:1 configuration and the other two 1:3:3 configurations.

V. Methods

Another aspect of the present disclosure can include methods 30, 40 (FIGS. 3 and 4) for applying photobiomodulation therapy (PBMT) proximal to an area of hemiplegia due to a stroke to improve functional mobility in a patient suffering from hemiplegia due to the stroke. The methods 30, 40 can be executed by hardware—for example, at least a portion of the system 10 shown in FIG. 1 and described above. Additionally, PBMT provides a non-pharmacological therapy to patients suffering from the effects of a prior stroke, which can be used alone or in combination with a pharmaceutical treatment or an alternative treatment (like rehabilitative exercise) to improve the patient's functional mobility.

The methods 30 and 40 are illustrated as process flow diagrams with flowchart illustrations. For purposes of simplicity, the methods 30 and 40 shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30 and 40. Additionally, one or more elements that implement the methods 30 and 40, such as light source device 11 and/or controller 12 of FIG. 1, may include a non-transitory memory and one or more processors that can facilitate the configuration and generation of the light signal.

Figure 3:
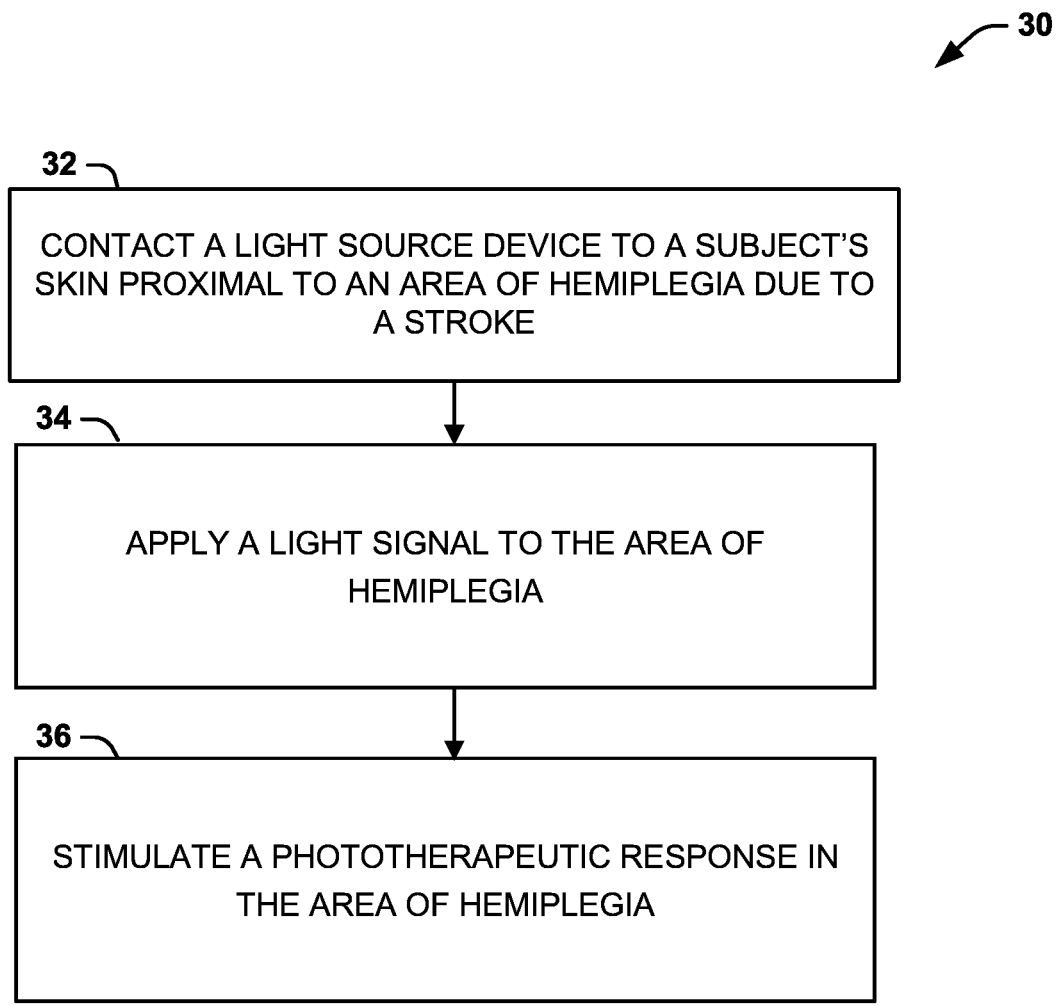
FIG. 3 is a process flow diagram of an example method for applying PBMT proximal to an area of hemiplegia within a subject due to a stroke to increase functional mobility in accordance with another aspect of the present disclosure.
Figure 4:
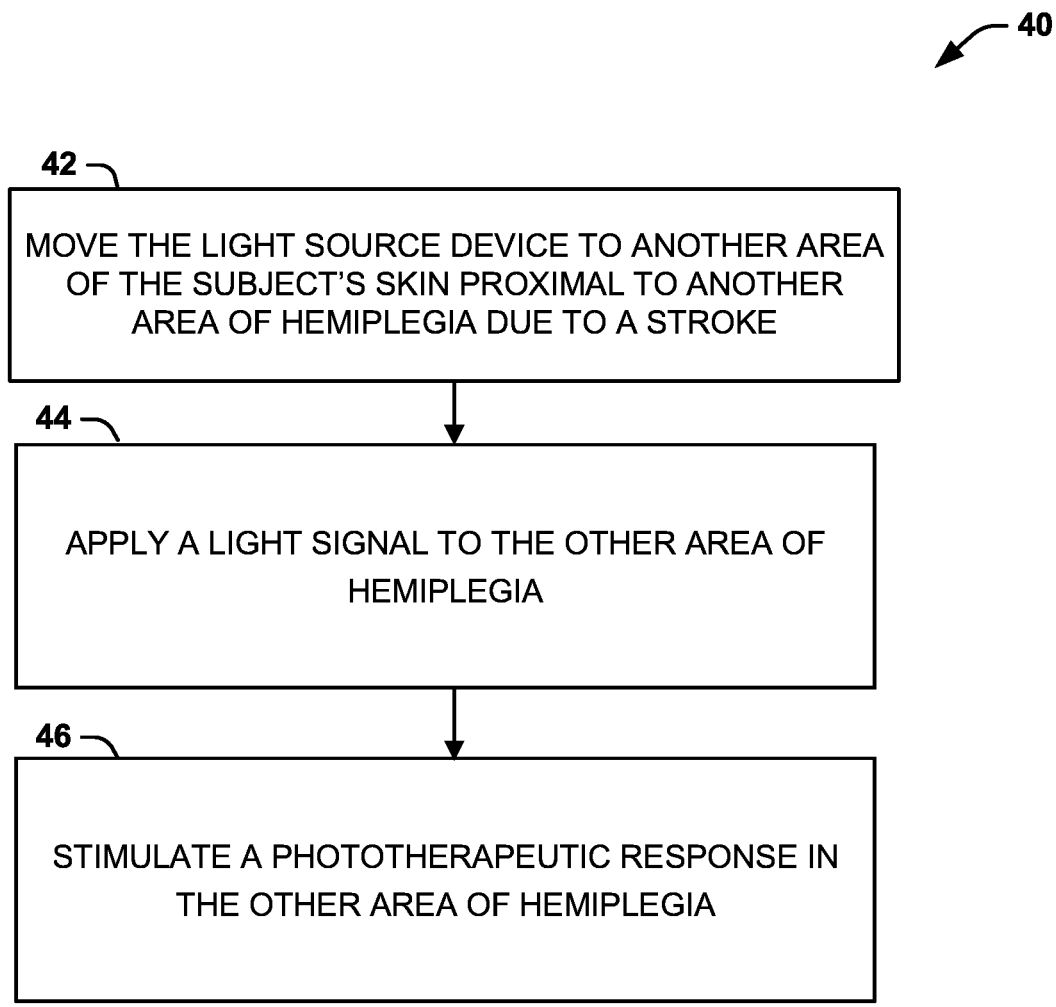
FIG. 4 is a process flow diagram of another example method for applying PBMT to another area of hemiplegia within a subject's body to increase functional mobility in accordance with a further aspect of the present disclosure.

Referring now to FIG. 3, shows a method 30 for applying PBMT proximal to an area of hemiplegia due to a stroke. At step 32, a light source device (e.g. light source device 11) can be contacted to a subject's skin proximal to (e.g., directly adjacent or over) the area of hemiplegia. The subject can be any patient who has experienced a stroke and/or suffers from hemiplegia.

At step 34, a light signal can be applied to the area of hemiplegia. The light signal can be generated by one or more light sources operating in at least one of a pulsed operating mode, a continuous operating mode, and/or a super-pulsed operating mode. The light signal can include one wave of a single wavelength. However, alternatively, the light signal can include a plurality of individual waves with multiple wavelengths. The combination of the plurality of individual waves can work constructively to create a synergistic effect, enhancing each individual wavelength's ability to penetrate the skin, allowing for a greater portion of the available light energy to reach biological targets beneath the surface of the skin. The light signal is applied for a time sufficient to stimulate a phototherapeutic response in the area of hemiplegia. At step 36, a phototherapeutic response can be stimulated in the area of hemiplegia. The phototherapeutic response can trigger a biological response in muscles and/or nerves of the area of hemiplegia, leading to an improvement in functional mobility and a corresponding improvement in a subject's overall quality of life The method 30 continues in FIG. 4, which shows a method 40 that occurs after moving the light source device. At step 42, the light source (e.g. light source device 11) can be moved to another area of the subject's skin proximal to another area of hemiplegia due to the stroke. The other area of hemiplegia can include another muscle, another nerve, and/or the same muscle/nerve. At step 44, a light signal can be applied to the other area of hemiplegia. At step 46, a phototherapeutic response can be stimulated in the other area of hemiplegia. The phototherapeutic response, in some instances, can be a sum of the phototherapeutic response between the different areas of hemiplegia to increase the functional mobility of the stroke patient (e.g., by reducing the hemiplegia through the stimulation of the nerves and/or muscles due to the PBMT).

VI. Experimental

The following example is shown for the purpose of illustration only and is not intended to limit the scope of the appended claims. This experiment demonstrates the promise of photobiomodulation therapy (PBMT), with a combination of different light sources (laser and LED) and a static magnetic field (sMF), to enhance the functional mobility in stroke survivors. The energy of 30 J per site was found to result in a significant increase in the distance traveled on the Six Minute Walk Test (6 MWT) and time required to complete the Timed Up and Go (TUG) test compared to a sham (0 J). The energy of 10 J and 50 J per site also showed improvement related to the distance traveled for the 6 MWT and the TUB test compared to the sham (0 J).

Methods
Study Design

A randomized, placebo-controlled, triple-blind, and crossover clinical trial was conducted in accordance with the Declaration of Helsinki and the guidelines for research involving human subjects. This study received approval from the Human Research Ethics Committee and was registered at the clinicaltrials.gov. All volunteers received clarifications regarding the objectives and procedures and signed a statement of informed consent of agreement. Moreover, the patients were informed that they could drop-out of the study at any time with no negative consequences.

Patients

The patients were adults recruited from the physical therapy clinics of the University (Universidade Nove de Julho) diagnosed with hemiparesis stemming from an ischemic or hemorrhagic stroke. Patients were blinded to the hypothesis and the type of PBMT+ magnetic field they were receiving.

Inclusion/Exclusion Criteria

Patients with a medical diagnosis of a single stroke event who met the eligibility criteria were included. Males and females aged 45-60 years with hemiparesis stemming from a single stroke event with crural predominance having occurred between six months and five years prior and receiving conventional standardized physical therapy treatment at University clinics were included. Other inclusion criteria were the ability to walk barefoot with or without a gait-assistance device (cane), controlled and clinically stable disease, ability to perform the 6MWT and TUG Test, capacity to read and understand the patient information chart, and the capacity to sign an informed consent statement. Patients with fixed deformities of the lower limbs, a history of osteoarticular disorders, any other health condition that would affect gait performance, or cognitive deficits that would affect the performance of the tests; those having undergone surgery; and those who did not meet the inclusion criteria were excluded from the study.

Sample Size

Since no previous studies determined the effects of PBMT/sMF on the functional mobility in stroke survivors, the number of patients per group was calculated based on the results of a pilot study involving three patients per group recently conducted by our research group to estimate the sample size. The calculation was made considering a β value of 20% and α value of 5%. The choice of the total energy delivered per site of 30 J for the procedure in the pilot study was based on a previous investigation that demonstrated the positive effects of PBMT/sMF on the skeletal muscle performance of healthy individuals. In the pilot study, the administration of PBMT/sMF resulted in a distance travelled on the 6MWT of 256.67 m (±44.24 m), whereas sham (0 J) PBMT/sMF resulted in a distance of 197.67 m (±59.18 m). The DSS Research was used for the calculation of sample size: https://www.dssresearch.com/resources/calculators/sample-size-calculator-average/

Using the parameters listed above, a minimum of 10 patients per group was determined. Since the study has a crossover design, this represents the total number of patients. However, 12 patients were recruited to compensate for a possible 20% dropout rate. As the PBMT device used in the study does not cause any harmful thermal effect in any skin tone, patients with different skin tones were recruited.

Blinding

All clinical assessments were conducted by an examiner blinded to the treatment allocation. Neither the investigator nor the patients were aware of whether a placebo or active treatment was being administered. The same PBMT/sMF device was used in all groups and the treatments were administered by a blinded therapist. The statistician involved in the main statistical analyses was blinded to the group allocation until the end of the statistical analyses. Only the researcher in charge of the randomization process and programming of the PBMT/sMF device had the identifying code to determine which treatment should be given.

Randomization

The patients received four PBMT/sMF total energies delivered per site over four weeks (sham—0J), 10J, 30J, and 50J). The order of treatments was randomized. We generated codes through the random.org website to ensure that at session 1, 1:1:1:1 of our patients received the total energy delivered per site of sham (0 J), 10 J, 30 J, and 50 J, respectively. The other sessions (2, 3, and 4) also had 25% of patients per dose, in order to counterbalance the patients between the energies tested (sham—0 J), 10 J, 30 J, and 50 J per site) during the 4 sessions (one dose each week). All patients started and finished the treatment at the same time; the randomization was balanced (3:3:3:3) ensuring the distribution of doses according of the week.

Randomization was performed to determine the order of the sham (0 J), 10 J, 30 J, and 50 J total energy delivered per site of PBMT/sMF to be applied from the first session. Patients received a different dose in each week, according to the randomization, successively during the 4 weeks of treatment. Labels were created according the randomization procedure through the random.org website, and a series of sealed, opaque, and numbered envelopes were created to ensure confidentiality. In the first session, each patient was grouped using a simple lottery system (A, B, C, and D) which determined the order of doses in which the patients in the 4 sessions would receive PBMT/sMF each week: A (sham—0 J), 10 J, 30 J, and 50 J), B (10 J, 30 J, 50 J and sham—0 J), C (30 J, 50 J, sham—0 J, and 10 J) and D (50 J, sham—0 J, 10 J, and 30 J). The PBMT/sMF unit used in the study emitted the same sounds independent of the dose or mode (active or sham—0 J) programmed. The randomization procedure was performed by a researcher who had the role of programming the device in accordance with the results of the randomization process. This researcher was instructed not to communicate the PBMT/sMF dose to any of the patients or other researchers involved until the end of the study. Thus, the researcher in charge of the PBMT/sMF had no knowledge regarding the doses administered to the patients.

Outcomes

The outcome measures used in this study have been previously validated in the literature. The examiners, therapists, and patients were blinded to the allocation of patients to different treatments as mentioned previously. Evaluations were performed on five occasions: 1) pre-intervention (baseline), 2) after sham (0 J), 3) after 10 J, 4) after 30 J, and 5) after 50 J total energy delivered per site. A member of the research team who did not interact with patients in the interventions or evaluations exported the data to spreadsheets and sent the data to the statistician.

Primary outcome: The 6MWT is a reliable test for post-stroke patients. Beginning from the standing position, the patients were instructed to walk at a self-selected pace without running for six minutes back and forth along a 10-meter track. The pace may vary, and the patients can stop briefly to rest, if needed. The distance in meters was recorded. The test was standardized according to the American Thoracic Society guidelines.

Secondary outcome: The TUG test it is a simple and rapid functional mobility test, based on the time (in seconds), which can concurrently measure basic movement and balance abilities. The method is to mark a 3-meter distance with one side having a standardized chair without an armrest and fixed to the ground. The patients were requested to sit on the chair, stand up, walk three meters, turn around, walk back to the chair, and sit down again. The total time it took for the subject to stand up, walk for 3 meters to the marked end, turn back, walk back, and sit back on the chair was calculated.

Intervention

PBMT/sMF was administered after the pre-intervention (baseline) evaluation and the total energy delivered per site for each week was determined based on the results of the randomization procedure. PBMT/sMF was administered in direct contact with the skin and applied with slight pressure to nine sites on the knee extensors, six sites on the knee flexors, and two sites on the plantar flexor muscles on both lower limbs.

PBMT/sMF was administered using a cluster of 12 diodes: four laser diodes of 905 nm (mean power of 0.3125 mW and peak power of 12.5 W for each diode), four LED diodes of 875 nm (mean power of 17.5 mW for each diode), four LED diodes of 640 nm (mean power of 15 mW for each diode), and a magnetic field of 35 mT. The device is manufactured by Multi Radiance Medical® (Solon, Ohio, USA). The cluster used in this study is circular and has an area of 20 cm2. Based on the randomization results, the patients received PBMT/sMF with the following total energies delivered per site: 10 J per site (76 seconds of irradiation in each site), 30 J per site (228 seconds of irradiation in each site), 50 J per site (380 seconds of irradiation in each site), or sham (0 J) (150 seconds of placebo irradiation in each site and no effective irradiation). The PBMT/sMF was applied with one-week interval washout between the doses.

Statistical Analysis

The intention-to-treat analysis was followed a priori. The researcher that performed statistical analysis was blinded to randomization and allocation of patients in experimental groups. The Shapiro-Wilk test was used to verify the normal distribution of data. Parametric data were expressed as means and standard deviations. Nonparametric data were expressed as medians and interquartile intervals. The data from the 6MWT and TUG tests were expressed as mean and standard deviation (±SD) and their percentage of change based on the values established in the baseline (±SEM). Two-way repeated measures ANOVA with intra-patient data and Bonferroni post hoc test were used for the comparisons. The statistical analysis was performed using Prisma 6 for IOS, with the level of significance set to 5% ($p<0.05$). The data are expressed as mean (±SD) in the tables, and as mean (±SEM) in graphs to allow better presentation of data.

Results

The following results demonstrate that PBMT with different light sources (laser and LED) and wavelengths in combination with sMF with a total energy per site of 30 J has positive acute effects on functional mobility in stroke survivors.

Among the 12 patients recruited for the present study, two dropped out without explaining their reasons. Thus, the sample was composed of ten patients, with a mean age of 58.5 years (plus or minus 10.04 years), 6 male/4 female, mean time since stroke 42.2 months (plus or minus 19.4), 5 ischemic/5 hemorrhagic stroke, 4 right side affected/6 left side affected.

Figure 5:
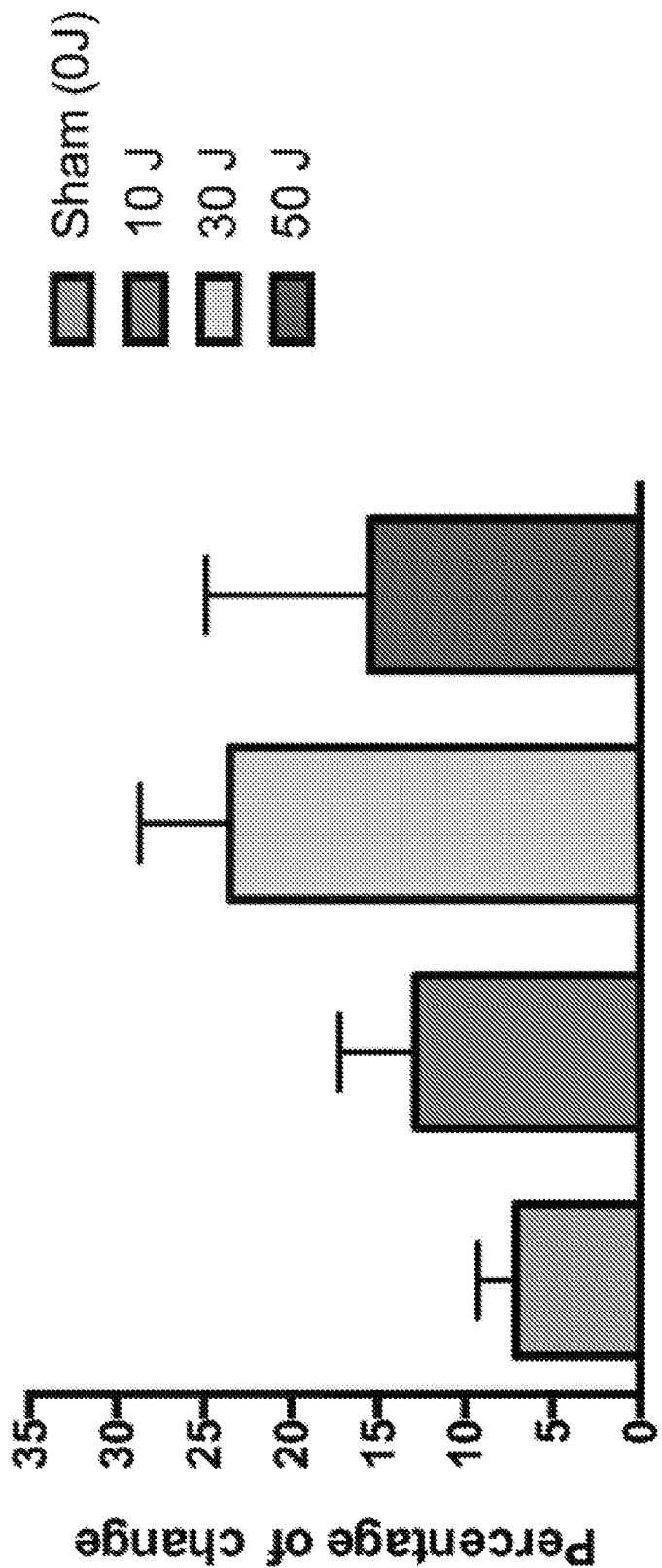
FIG. 5 shows graphs illustrating a percentage change in the distance achieved during a six-minute walking test for different energies of PBMT applied.

FIG. 5 displays the percentage of change from baseline for the 6MWT. There were no statistical differences in the energies tested (p>0.05) (mean/SEM: Sham (0 J)=7.02/ 6.862; 10 J=12.85/13.89; 30 J=23.50/16.39 and 50 J=15.41/ 29.98).

Figure 6:
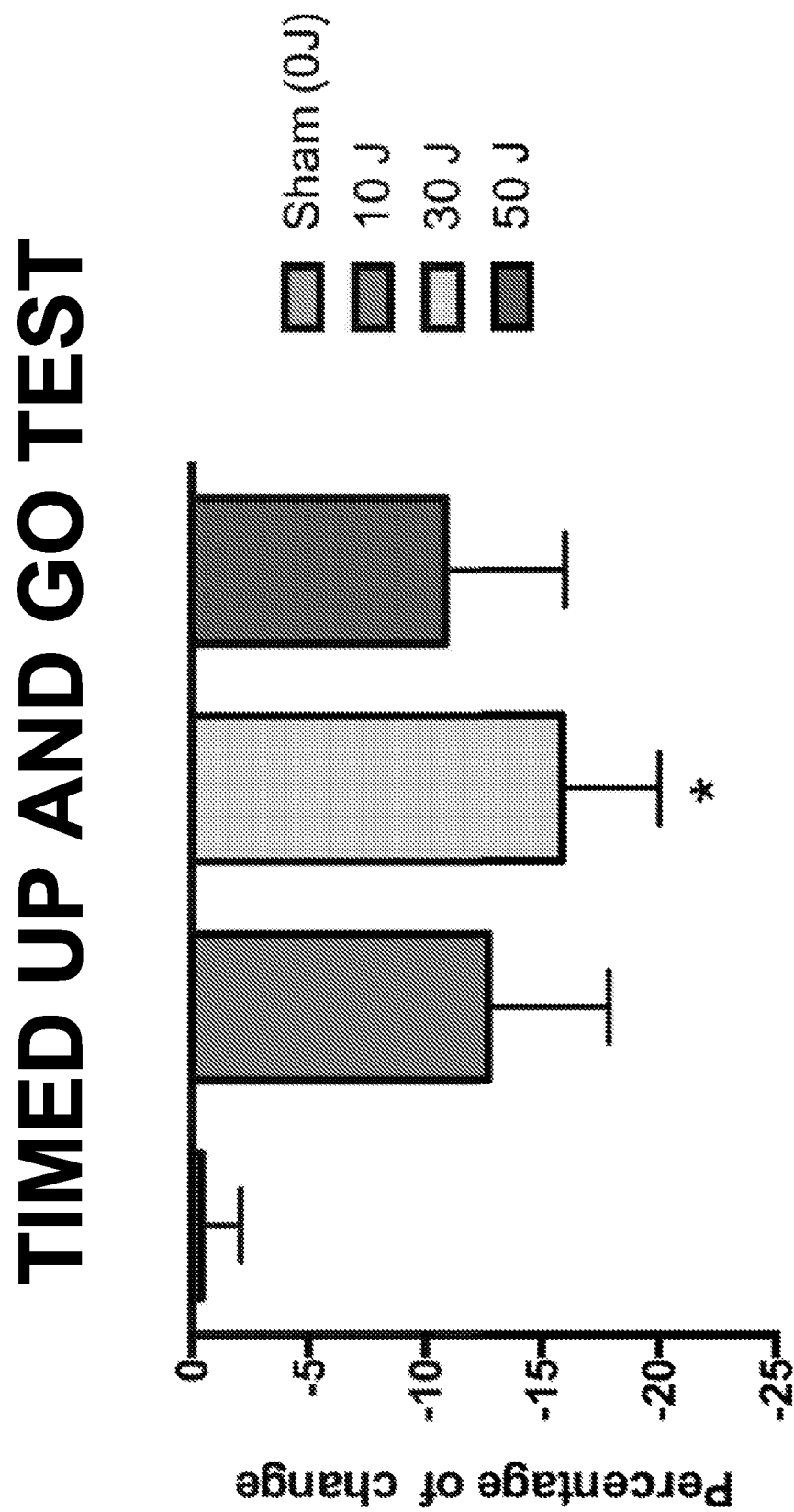
FIG. 6 shows a graphs illustrating a percentage change in TUG for different energies of PBMT applied.

FIG. 6 displays the percentage of change from baseline for the TUG test, compared to sham (0 J), the PBMT/sMF with 30 J per site showed statistically significant improvements (p<0.05), (mean/SEM: Sham (0 J)=−0.4110/5.319; 10 J=−12.71/16.31; 30 J=−15.87/13.16 and 50 J=−10.85/ 16.29).

This is the first study to evaluate the acute effects, optimal dose, and the applicability of PBMT with a combination of different light sources (laser and LED) and sMF on the functional mobility in stroke survivors. The energy of 30 J per site (510J per lower limb) was found to result in a significant increase in the distance travelled on the 6MWT compared to the baseline (p<0.01) and sham (0 J) (p<0.05). This same dose also had a positive effect on the TUG, with a significant decrease in the time required to execute the test in comparison to both baseline and sham (0 J) (p<0.05). Moreover, this same energy also had a positive effect on the TUG, in relation to percentage of change compared to baseline (p<0.05).

Both the distance travelled on the 6MWT (measured in meters) and the time required to execute the TUG test (measured in seconds) adequately reflect the physical capacity of patients to perform routine tasks and both tests are widely used in clinical practice for the evaluation of functioning inpatients or to evaluate the effects of an intervention.

Post-stroke muscular dysfunction is likely a multi-factorial phenomenon that includes contributions from reduced physical activity and compensatory motor patterns that lead to muscle atrophy and weakness. In a clinical point of view, paretic muscle atrophy strongly correlates with decreased gait speeds and reduced functional mobility in individuals following a stroke. Reduction in functional mobility encourages a sedentary lifestyle leading to an increased risk of cardiac events or recurrent stroke and reduced quality of life. Thus, there is a critical need to enhance the functional mobility outcomes post-stroke. As mentioned previously, improvements in the functional mobility through of measures were found 6MWT and TUG test with the administration of PBMT/sMF at an energy of 30 J per site (510 J per limb) in the present study when compared to both the baseline evaluation and sham (0 J) treatment.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A method comprising:
contacting a light source device to a subject's skin proximal to an area of hemiplegia within a subject due to a stroke;
applying a light signal in at least one of a pulsed operating mode, a continuous operating mode, and a super-pulsed operating mode through the light source device to the subject's skin proximal to the area of hemiplegia, wherein the light signal is applied for a time sufficient to stimulate a phototherapeutic response in at least one muscle proximal to the area of hemiplegia,
moving the light source device to contact another area of hemiplegia within a subject due to a stroke; and
applying another light signal in at least one of the pulsed operating mode, the continuous operating mode, and the super-pulsed operating mode through the light source device to the subject's skin proximal to the other area of hemiplegia within the subject due to the stroke, wherein the other light signal is applied for a time sufficient to stimulate another phototherapeutic response in at least one muscle proximal to the other area of hemiplegia within the subject due to the stroke.

2. The method of claim 1, wherein the muscles proximal to the area of hemiplegia comprises at least one knee flexor muscle or at least one plantar flexor muscle.

3. The method of claim 1, wherein the phototherapeutic response improves at least one of functional mobility, spatiotemporal and kinematic gate variables, static balance, and muscle activity exhibited by the subject.

4. The method of claim 1, wherein the light source device is a probe device or a flexible array device.

5. The method of claim 1, wherein the light signal comprises at least two lights produced by at least two different light sources with at least two different wavelengths, wherein the at least two different light sources are within the light source device.

6. The method of claim 5, wherein at least one of the lights is produced in the super-pulsed operating mode.

7. The method of claim 1, wherein the applying further comprises applying the light signal so that from 10 J to 50 J of energy is received at the area of hemiplegia.

8. The method of claim 1, wherein the applying further comprising applying the light signal so that 30 J of energy is received at the area of hemiplegia.

9. The method of claim 1, wherein the light source device is a portable device comprising a power source that is removably securable to the area of the subject's skin.

10. The method of claim 1, wherein the light source device comprises at least three light sources each configured to apply a portion of the light signal comprising a different wavelength within a wavelength range of 600-1100 nm, wherein each of the at least three light sources operates in the pulsed operating mode, the continuous operating mode, or the super-pulsed operating mode.

11. The method of claim 10, wherein the at least three sources comprise a first source configured to generate a first portion of the light signal with a wavelength from 890-910 nm, a second source configured to generate a second portion of the light signal with a wavelength from 600-700 nm, and a third source configured to generate a third portion of the light signal with a wavelength from 810-910 nm, wherein the first light source operates in the super-pulsed operating mode, the second light source operates in the pulsed operating mode or the continuous operating mode, and the third light source operates in the pulsed operating mode or the continuous operating mode.

12. The method of claim 11, wherein the first light source comprises a super pulsed laser that creates an impulse of high intensity that emits for a billionth of a second in synchrony with the third light source.

13. The method of claim 11, wherein the first light source comprises a super-pulsed infrared laser source, the second light source comprises a red light source, and the third light source comprises an infrared light source.

14. The method of claim 11, wherein the light source device further comprises a permanent magnet that provides a constant magnetic field from 5 mT to 1 T.

* * * * *